United States Patent [19]

Chan

[11] Patent Number: 4,696,940

[45] Date of Patent: Sep. 29, 1987

[54] METHOD FOR TREATING HYPERTENSION USING 3-(4-IMIDAZOLYLMETHYLENE)-CARBAZIC AND DITHIOCARBAZIC ACID ESTERS

[75] Inventor: Peter S. Chan, Suffern, N.Y.

[73] Assignee: American Cyanamid Company, Stamford, Conn.

[21] Appl. No.: 924,394

[22] Filed: Oct. 29, 1986

[51] Int. Cl.$^4$ .......................................... A61R 31/415
[52] U.S. Cl. .................................................... 514/400
[58] Field of Search ........................................ 514/400

[56] References Cited

U.S. PATENT DOCUMENTS 4,124,766  11/1978  Paul et al. ............................ 544/184

Primary Examiner—Allen J. Robinson
Attorney, Agent, or Firm—Edward A. Conroy, Jr.

[57] ABSTRACT

This disclosure describes compositions of matter containing substituted 3-(4-imidazolymethlene)carbazic and dithiocarbazic acid esters and the method of treating hypertension therewith.

9 Claims, No Drawings

METHOD FOR TREATING HYPERTENSION USING 3-(4-IMIDAZOLYLMETHYLENE)-CARBAZIC AND DITHIOCARBAZIC ACID ESTERS

SUMMARY OF THE INVENTION

This invention is concerned with a method of treating hypertension in mammals by the administration of a compound selected from those of the formula:

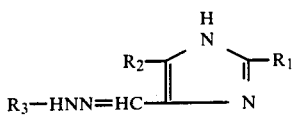

wherein $R_1$ is selected from the group consisting of straight oR branched chain alkyl($C_1$-$C_6$), methoxymethyl and benzyl; $R_2$ is selected from the group consisting of hydrogen and methyl; and $R_3$ is selected from the group consisting of

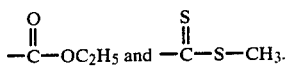

BACKGROUND OF THE INVENTION

The 3-(4-imidazolylmethylene)carbazic and dithiocarbazic acid esters of the above formula are disclosed and claimed either generically or specifically in U.S. Pat. No. 4,124,766, together with methods for their preparation and disclosure as intermediates for the preparation of compounds which inhibit the enzyme cyclic-AMP phosphodiesterase.

DESCRIPTION OF THE INVENTION

The compounds of the present invention are active hypotensive agents as established in the following test described by P. S. Chan and D. W. Poorvin, Clinical and Experimental Hypertension, 1(6), 817–830 (1979).

Male, 16 week old, spontaneously hypertensive rats of the Okamoto strain, having an average mean arterial blood pressure (MABP) of 160±1.5 mm of mercury, are used in this test. Normally, one to three rats are used per test compound. A rat is dosed by gavage with a test compound, suspended in 2% preboiled starch, at a concentration of 50 mg/ml, at the indicated dose, with 0.9% sodium chloride loading at a dose of 25 ml/kg of body weight. A second identical dose of the test compound, without sodium chloride loading, is given 24 hours later. At 28 hours after the initial dose, the mean arterial blood pressure is measured. The procedure is repeated in a second and third rat when necessary.

The results of this test on representative compounds of this invention appear in Table I.

TABLE I

| Compound | Hypotensive Activity | | |
|---|---|---|---|
| | Dose (mg/kg) | MABP (mmHg) | No. of Rats |
| 3-[2,5-Dimethyl-4-imidazolyl)-methylene]carbazic acid, ethyl ester | 100 | 133 | 1 |
| 3-[(2-Benzyl-4-imidazolyl)-methylene]carbazic acid, ethyl ester | 100 | 130 | 1 |
| 3-[(2,5-Dimethyl-4-imidazolyl)-methylene]dithiocarbazic acid, methyl ester | 50 | 123 | 2 |
| 3-(5-Methyl-2-propyl-4-imidazolylmethylene)carbazic acid, ethyl ester | 100 | 125 | 2 |
| 3-[[2-(Methoxymethyl)-4-imidazolyl]methylene]dithiocarbazic acid, methyl ester | 50 | 140 | 1 |
| 3-[(2-tert.-Butyl-5-methyl-4-imidazolyl)methylene]carbazic acid, ethyl ester | 100 | 120 | 2 |

The compounds of this invention have thus been found to be highly useful for treating hypertension in mammals when administered in amounts ranging from about 5 mg to about 100 mg/kg of body weight per day. Such dosage units are employed that a total of from about 0.35 g to about 3.5 g of active compound for a subject of about 70 kg of body weight are administered in a 24 hour period. The dosage regimen may be adjusted to provide the optimum therapeutic response. For example, several divided doses may be administered daily or the dose may be proportionally reduced as indicated by the exigencies of the therapeutic situation.

A decided practical advantage is that these compounds may be administered by the oral route, for example, with an inert diluent or with an assimilable edible carrier, or they may be enclosed in hard or soft shell gelatin capsules, or they may be compressed into tablets, or they may be incorporated directly with the food of the diet.

For oral therapeutic administration, the active compounds may be incorporated with excipients and used in the form of tablets, capsules, elixirs, suspensions, syrups and the like. Such compositions and preparations should contain at least 0.1% of active compound and normally this varies between 2% and 60% of the weight of the unit, such that a suitable dosage is obtained.

The tablets, capsules and the like may also contain a binder such as gum tragacanth, acacia, corn starch or gelatin; excipients such as dicalcium phosphate; a disintegrating agent such as alginic acid; a lubricating agent such as magnesium stearate; and a sweetening agent such as sucrose, lactose or saccharin or a flavoring agent such as peppermint, oil of wintergreen or cherry flavoring.

When the dosage unit is a capsule it may contain, in addition to materials of the above-type, a liquid carrier such as a fatty oil.

Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propylparabens as preservatives, a dye and flavoring such as cherry or orange flavor.

All materials used must be pharmaceutically pure and substantially non-toxic in the amounts employed.

EXAMPLE 1

Preparation of 50 mg Tablets

| Per Tablet | Ingredient | Per 10,000 Tablets |
|---|---|---|
| 0.050 g | 3-[(tert.-Butyl-5-methyl-4-imidazolyl)methylene]carbazic acid, ethyl ester | 500 g |
| 0.080 g | Lactose | 800 g |
| 0.010 g | Corn starch (for mix) | 100 g |
| 0.008 g | Corn starch (for paste) | 80 g |
| 0.148 g | | 1480 g |
| 0.002 g | Magnesium stearate | 20 g |
| 0.150 g | | 1500 g |

The 3-[(2-tert.-butyl-5-methyl-4-imidazolyl)-methylene]carbazic acid, ethyl ester, lactose and corn starch for mix are blended together. The corn starch (for paste) is suspended in 600 ml of water and heated with stirring to form a paste. This paste is then used to granulate the mixed powders. The wet granules are screened, dried at 120° F. and then rescreened. The mixture is lubricated with magnesium stearate and compressed into tablets.

EXAMPLE 2

Preparation of Oral Suspension

| Ingredient | Amount |
|---|---|
| 3-[(2,5-Dimethyl-4-imidazolyl)-methylene]dithiocarbazic acid, methyl ester | 500 mg |
| Sorbitol solution (70% N.F.) | 40 ml |
| Sodium benzoate | 150 mg |
| Saccharin | 10 mg |
| Red dye | 10 mg |
| Cherry flavor | 50 mg |
| Water qs | 100 ml |

The sorbitol solution is added to 40 ml of water and the 3-[(2,5-dimethyl-4-imidazolyl)methylene]dithiocarbazic acid, methyl ester is suspended therein. The saccharin, sodium benzoate, flavor and dye are added and dissolved. The volume is adjusted to 100 ml with water. Each ml of suspension contains 5 mg of active compound.

I claim:

1. A method of treating hypertension in a mammal in need of said treatment which comprises administering to said mammal a hypotensive effective amount of a compound of the formula:

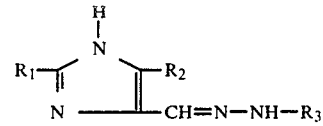

wherein $R_1$ is alkyl($C_1$-$C_6$), methoxymethyl or benzyl; $R_2$ is hydrogen or methyl; and $R_3$ is a moiety of the formulae:—$CO_2C_2H_5$ or —$CS_2CH_3$.

2. The method according to claim 1 wherein the compound is 3-[(2,5-dimethyl-4-imidazolyl)methylene]-carbazic acid, ethyl ester.

3. The method according to claim 1 wherein the compound is 3-[(2-benzyl-4-imidazolyl)methylene]carbazic acid, ethyl ester.

4. The method according to claim 1 wherein the compound is 3-[(2,5-dimethyl-4-imidazolyl)methylene]-dithiocarbazic acid, methyl ester.

5. The method according to claim 1 wherein the compound is 3-[(5-methyl-2-propyl-4-imidazolyl)methylene]carbazic acid, ethyl ester.

6. The method according to claim 1 wherein the compound is 3-[(2-methoxymethyl-4-imidazolyl)methylene]-dithiocarbazic acid, methyl ester.

7. The method according to claim 1 wherein the compound is 3-[(2-tert.-butyl-5-methyl-4-imidazolyl)methylene]carbazic acid, ethyl ester.

8. The method according to claim 1 wherein the compound is 3-[(2-benzyl-5-methyl-4-imidazolyl)methylene]carbazic acid, ethyl ester.

9. A therapeutic composition in the form, of tablets, capsules, elixers, suspensions and syrups for treating hypertension in mammals, comprising from about 5 mg. to about 500 mg of a compound of claim 1 in association with a pharmaceutically acceptable carrier.

* * * * *